United States Patent [19]

Aubert et al.

[11] Patent Number: 4,942,033
[45] Date of Patent: Jul. 17, 1990

[54] VEGETABLE EXTRACT-BASED COSMETIC OR PHARMACEUTICAL COMPOSITION WHICH ACTS ON CAPILLARY BRITTLENESS

[75] Inventors: Lucien Aubert, Cap-D'Ail; Philippe Anthoine, Nice, both of France

[73] Assignee: L'Oreal, Paris, France

[21] Appl. No.: 896,570

[22] Filed: Aug. 15, 1986

Related U.S. Application Data

[63] Continuation of Ser. No. 686,836, Dec. 27, 1984, abandoned.

[30] Foreign Application Priority Data

Dec. 27, 1983 [FR] France ................ 83 20826

[51] Int. Cl.$^5$ .............................. A61K 35/78
[52] U.S. Cl. ................................. 424/195.1
[58] Field of Search ...................... 424/195.1

[56] References Cited

FOREIGN PATENT DOCUMENTS 2104911 4/1972 France ............................ 424/195.1
2377201 8/1978 France ............................ 424/195.1
7701290 8/1978 France ............................ 424/195.1

OTHER PUBLICATIONS

Chemical Abstracts, vol. 81, No. 12, Sep. 23, 1984, p. 328, No. 68366b.
Chem. Abst. 91:9494a, 1979.
Chem. Abst. 78:90820c, 1973.
Chem. Abst. 82:83016b, 1975.
Merck Index, 9th ed., No. 1248, 1980.

Primary Examiner—John W. Rollins
Attorney, Agent, or Firm—Oliff & Berridge

[57] ABSTRACT

A composition for cosmetic or pharmaceutical use is disclosed. The composition contains a cosmetically or pharmaceutically acceptable carrier, and a combination of vegetable extracts comprising:
(i) a fragon extract (*Ruscus aculeatus* L.), and
(ii) a sage extract (*Salvia officinalis* L.).

The composition can be used for the treatment of capillary brittleness by reducing capillary permeability and by increasing capillary resistance.

8 Claims, No Drawings

VEGETABLE EXTRACT-BASED COSMETIC OR PHARMACEUTICAL COMPOSITION WHICH ACTS ON CAPILLARY BRITTLENESS

This is a continuation of application Ser. No. 686,836 filed December 27, 1984, now abandoned.

BACKGROUND OF THE INVENTION

This application pertains to a new composition, which can be used in the cosmetic or pharmaceutical field, that contains vegetable extracts and which acts on the capillaries by reducing their permeability and increasing their resistance.

Extracts of *Ruscus aculeatus* L. which are either isolated or associated with a vitamin factor have been recommended for treatment of functional problems in connection with venous insufficiency and capillary brittleness. Also, fractions which are enriched with stabilized *Ruscus aculeatus* L. rhizome saponins have been described as having therapeutic activity especially with venous disorders, varicose veins, ulcers, hemorrhoids and various disorders in the capillary system such as purpura, epistaxis, chilblains or gynecological disorders.

The prior art compositions are generally described in French patent No. 77/01290 as well as in B.S.M. No. 3,994.M.

SUMMARY OF THE INVENTION

After various studies on *Ruscus aculeatus* L. extracts, it was found that it is possible to obtain a complementary synergy of activity in the reduction of capillary permeability and in the increase of capillary resistance, by linking *Ruscus aculeatus* L. extracts with sage or *Salvia officinalis* L. extracts. Also, by linking these extracts with passiflore or passion-flower (*Passiflora incarnata*) extracts the synergy of activity can be increased substantially and the activity was found to be more constant over a period of time.

Therefore, the present invention pertains to a cosmetic or pharmaceutical composition which acts on capillaries by reducing their permeability and by increasing their resistance. The composition of the present invention contains in a suitable cosmetic or pharmaceutical carrier, a combination of vegetable extracts comprising:

(i) a fragon extract (*Ruscus aculeatus* L.), and
(ii) a sage extract (*Salvia officinalis* L.).

According to the invention, this combination of vegetable extracts exists in a composition with the following concentrations, as expressed in dry matter:

| | |
|---|---|
| dry extract of fragon (*Ruscus aculeatus* L.) | 0.1 to 3% |
| and preferably | 0.3 to 2.5% |
| dry extract of sage (*Salvia officinalis* L.) | 0.01 to 5% |
| and preferably | 0.3 to 3.5% |

According to a preferred embodiment, the composition can also contain a soft extract of passiflore (*Passiflora incarnata*) with a concentration (expressed as solid matter)

| | |
|---|---|
| of from | 0.1 to 2% |
| and preferably from | 0.2 to 1.5% |

The vasoprotective effect of these combinations as well as their synergy of activity were highlighted by the petechia method which will be described below.

DETAILED DESCRIPTION

The dry extract of fragon or butcher's broom (*Ruscus aculeatus* L.), which is used in the compositions of the present invention, is obtained from rhizomes which have been previously ground and extracted with a hydro-alcoholic solution of an alcohol containing 3 to 6 carbon atoms, and preferably with water-saturated n-butanol.

Representative extract methods are described in French patent Nos. 1,377,453, 69/23340 and 71/29817, the latter patent pertaining especially to the purification of extracts which are obtained for the purpose of enriching them with saponins.

*Ruscus aculeatus* L. extracts obtained from these methods appear as a tan powder which is 2% soluble in water and in alcohol at 60° C. The extracts have at least a 65% saponin content and preferably have a saponin content of from 70 to 80%.

The dry sage or *Salvia officinalis* L. extract is an extract that is obtained from leaves and dried flowery extremities. Extraction can be achieved in hot water. The extraction juices are then filtered, concentrated under vacuum and then dried by atomization. According to the present invention hydro-alcoholic extracts, tinctures containing 60 or 40% alcohol, fluid alcoholic (30%) or propylene-glycolic (40%) extracts can be used.

The dry sage extract is generally characterized by the presence of ursolic acid, flavonoids (lutenolin and apigenin glucosides), rosmarinic acid, picrosalvin as well as of various terpenic products such as tujone, borneol, salvene, pinene, bornyl acetate and linolyl acetate. The dry extract appears as a fine powder, having a color ranging from a yellowish brown to a brown. The dry extract is 1% soluble in water and slightly soluble in alcohol at 60° C. and barely soluble in alcohol at 95° C.

The soft passiflore or *Passiflora incarnata* extract is obtained by aqueous or hydro-alcoholic extraction of the above-ground sections of the plant, then through concentration to obtain a pasty mass having a solid content of greater than 60% and preferably about 80%. In terms of active principles, the extract which appears as a very dark brown paste contains vitexin, isovitexin, orientin and isoorientin. A 2% solution in 50% ethanol (by volume) is clear or slightly opalescent.

When the compositions of the present invention are intended for cosmetic applications, they preferably are prepared as an emulsion, a cream, a milk, a gel, a lotion, a poultice or an aerosol foam.

The compositions suitable for topical application have a thinning and anti-cellulite action especially when they are linked to other vegetable extracts and/or other active principles such as hydrosoluble organic compositions derived from mono methyl trisilanol such as mono methyl trisilanol manuronate which is sold by the EXYMOL Company as "Algisium" (aqueous solution containing 1% of mono methyl trisilanol manuronate) or the lactate which is sold by EXYMOL Company as "Lasilium" (aqueous solution which contains 1% of mono methyl trisilanol lactate). The latter compositions can be present in concentrations from 2 to 20% of 1% solutions or from 0.02 to 0.2% by weight expressed in active matter.

The compositions can contain other traditional ingredients such as perfumes, coloring agents, preservatives, thickeners and solvents.

According to a preferred embodiment of the present invention, the compositions are intended for pharmaceutical use in cases of venous or capillary insufficiency. The compositions especially are applied in phlebology and venous-related syndromes such as "heavy legs", leg ulcers, phlebitis, chilblains, in gynecology with respect to some dysmenorrheas, and in proctology for the treatment of simple hemorrhoids and hemorrhoidal anitis.

Pharmaceutical compositions which are intended for systemic application can be prepared, for instance, by adding extracts as defined above as active substances, to solid or liquid conventional non-toxic inert supports. These compositions can be administered enterally, parenterally or topically. With respect to enteral administration, the compositions are prepared in the form of pills, granules, capsules, lozenges, syrups, suspensions, solutions or suppositories. The dosage is obviously dependent on the method of administration and the desired activity.

For instance in proctology, suppositories might contain, per unit, in an excipient that is comprised of semi-synthetic glycerides:
0.01 to 0.05 g of dry sage extract,
0.01 to 0.03 g of dry fragon extract, and preferably:
0.01 to 0.03 g of soft passiflore extract.

Pharmaceutical compositions can contain inert additives or those which are possibly pharmaco-dynamically active. Pills or granules can contain binding agents, fillers, supports or diluents. Liquid compositions can be present for instance in the form of a sterile water miscible solution. In addition to extracts, capsules can contain a filler or thickening agent. Orally administered pharmaceutical compositions can also contain taste improving agents and substances which are generally used as preservatives, stabilizers, regulators and emulsifiers.

The supports and diluents mentioned above are comprised of organic or mineral substances, such as gelatin, lactose, starch, magnesium stearate, talcum, arabic gum or poly-alkylene-glycols. When pharmaceutical compositions are intended for topical applications, they are prepared in the form of ointments, pomades, tinctures, creams, solutions, lotions, sprays or suspensions. Ointments or pomades are preferred and they are prepared by mixing the extracts according to the invention as active consituents with inert non-toxic supports which are suitable for topical treatment.

For example, a cream used to treat heavy legs, periphlebitis, hypodermitis or chilblains, contains in an appropriate excipient for a 100 g sample,
0.3 to 3.5 h of dry sage extract, and
0.3 to 2.5 h of dry fragon extract, and preferably:
0.2 to 1.5 g of a soft passiflore extract.

Measuring Activity on Capillary Brittleness by the Petechia Method.

This method is commonly used to determine capillary brittleness and was described in the article by J. L. PARROT and P. CANU, "Factors which heighten the resistance of capillaries" Int. Pharmaco-dyn. Arch. No. 1, p. 152 (1964). The principle and method shall be explained below.

The principle involves inducing the appearance of petechiae on part of the back skin of rats with a vacuum chamber, which enables the measurement of capillary resistance where time=0. Then the composition to be tested is applied on an adjacent and defined skin zone which leads to a change in resistance of the capillary in that skin zone. The change in resistance is recorded on various parts of the skin which are treated at regular time intervals (30 min., 1 hr., 1 hr. 30 min., 2 hrs., 2 hrs. 30 min.). The experiment ends with a final measurement on part of the untreated skin to verify that the control measurement at time =0 did not change.

The apparatus enabling the measurement is derived from that which is described by R. CHARLIER, A. HOOSLET and M. COLOT, "Experimental investigations on vascular brittleness" Int. Arch. of "Physiology and Biochemistry", 71, (1), 1963. The apparatus includes a vacuum pump which is connected to a vacuum tank which is itself connected to a manometer that enables measurement of the vacuum expressed in mm of Hg. A flask is inserted between the vacuum tank and the manometer and acts as a buffer zone. A cell which is connected to a glass pipe controlled by a faucet enables the application of pressure onto the skin. The cell has a diameter of about 5 mm and it includes flat edges so as to prevent skin distortion.

For each composition to be tested, the measurements of capillary resistance were achieved on 16 WISTAR while male rats (weight 300–400 g) of which the lower dorsal section was shaved and depilated, and the animals were left resting for 48 hrs. prior to the experiment.

At the onset of experimentation, the capillary resistance threshold for each rat is measured by applying a vacuum of 300 mm of Hg for 15 seconds then by increasing such vacuum by 5 mm of Hg until petechiae appear (4 or 5 petechiae).

After this measurement is achieved, the composition to be tested is then applied (2 mg/cm$^2$) on an adjacent and defined section of skin and the vacuum required to produce petechiae in various sites is measured every 30 min. The experiment stops after the 6th measurement, or after 2 hrs. 30 min.

Then the capillary resistance of an untreated section is measured to verify, that the capillary resistance measured at time t=0 did not suffer any notable changes.

According to this method, capillary resistance was assessed with the following compositions:

| | | |
|---|---|---|
| (1) Placebo | = excipient with the following composition: | |
| Polyacrylic acid (Carbopol 941) | | 0.2 g |
| 99% Triethanolamine | | 0.6 g |
| Propylene glycol | | 5.0 g |
| Methyl parahydroxybenzoate | | 0.1 g |
| Propyl parahydroxybenzoate | | 0.2 g |
| Stearic acid | | 2.0 g |
| Self-emulsifying glycerol stearate | | 4.0 g |
| Cetyl alcohol | | 1.0 g |
| Vaseline oil | | 20.0 g |
| Sterile mineral-free water q.s.p. | | 100.0 g |
| (2) P cream | = Excipient + 0.5% of soft passiflore extract | |
| (3) S cream | = Excipient + 0.5% of dry sage extract | |
| (4) F cream | = Excipient + 1% of dry fragon extract | |
| (5) FP cream | = Excipient + 1% of dry fragon extract + 0.5% of soft passiflore extract | |
| (6) PS cream | = Excipient + 0.5% of soft passiflore extract + 0.5% of dry sage extract | |
| (7) FS cream | = Excipient + 1% of dry fragon extract + 0.5% of dry sage extract | |
| (8) FSP cream | = Excipient + 1% dry fragon extract + 0.5% of dry sage extract + 0.5% of soft passiflore extract | |

The results observed are depicted in Table A below. The values obtained (mm/Hg) correspond to an average of measurements recorded on 16 rats treated with each cream.

TABLE A

| (sample) | | 0 | ½ hr. | 1 hr. | 1½ hr. | 2 hr. (sample) | 2½ hr. | >2½ hr. |
|---|---|---|---|---|---|---|---|---|
| Placebo | 1* | 373.8 | 371.1 | 373.8 | 374.3 | 373.5 | 374.6 | 373.5 |
| | 2** | — | −0.7 | 0 | +0.4 | −0.1 | +0.2 | −0.1 |
| Cream P | 1 | 379.1 | 382.2 | 387.5 | 390.0 | 390.3 | 385.2 | 380.3 |
| | 2 | — | +0.8 | +2.2 | +2.9 | +3.0 | +1.8 | +0.3 |
| Cream S | 1 | 364.4 | 366.5 | 370.6 | 374.7 | 376.2 | 376.6 | 366.8 |
| | 2 | — | +0.6 | +1.7 | +2.8 | +3.3 | +3.3 | +0.6 |
| Cream F | 1 | 376.5 | 380.9 | 388.2 | 392.3 | 394.3 | 391.2 | 378.5 |
| | 2 | — | +1.1 | +3.1 | +4.2 | +4.8 | +3.9 | +0.5 |
| Cream FP | 1 | 367.8 | 375.0 | 388.7 | 394.4 | 403.7 | 405.3 | 374.4 |
| | 2 | — | +1.9 | +5.7 | +7.2 | +9.8 | +10.2 | +1.8 |
| Cream PS | 1 | 370.0 | 372.8 | 380.6 | 387.8 | 390.6 | 392.8 | 373.4 |
| | 2 | — | +0.8 | +2.9 | +4.8 | +5.6 | +6.2 | +0.9 |
| Cream FS | 1 | 378.1 | 399.8 | 417.2 | 432.3 | 442.8 | 454.1 | 381.9 |
| | 2 | — | +5.7 | +10.3 | +14.3 | +17.1 | +20.1 | +1.0 |
| Cream FSP | 1 | 390.9 | 397.8 | 424.4 | 455.0 | 480.9 | 481.9 | 403.4 |
| | 2 | — | +1.8 | +8.5 | +16.4 | +23.0 | +23.3 | +3.2 |

*1 = Average of values in mm of Hg
**2 = % of development in relation to the sample (t = 0).

ANALYSIS OF FINDINGS (1) The Placebo has no effect on capillary resistance.

(2) The soft passiflore extract very slightly increases capillary resistance (maximum of about 3% obtained after 2 hrs then a fast drop).

(3) The dry sage extract displays a maximum that is similar to the passiflore extract but it remains constant after 2 hrs.

(4) The dry fragon extract exercises notable activity on capillary resistance (about 4.5% between 1 hr and 2 hrs after being applied).

(5) The combination of fragon extract and passiflore extract exercises activity on capillary resistance, the latter rising to about 10% after 2 hrs–2 hrs 30 min. following application.

(6) The combination of soft passiflore extract and dry sage extract also displays an effect on capillary resistance but it is less pronounced (only 6% after 2 hrs 30 min.).

(7) The combination of dry fragon extract and dry sage extract has a significant synergistic effect on capillary resistance in relation to the dry fragon extract on the one hand and the dry sage extract on the other hand (increase of capillary resistance of about 20%).

(8) The combination of dry fragon extract, dry sage extract and soft passiflore extract induces a very high increase in capillary resistance.

If, with the averages which are recorded for each cream, the method of multiple comparison for averages by NEWMAN and KEULS (variance analysis) is applied, the ranks which are provided below are obtained. For a given time, the averages which were recorded for each cream are ranked in increasing order.

The averages which are underlined by a continuous line are not especially different from one another, otherwise the difference is significant with a 5% margin of error.

(1) Time 1 hr

| Cream | S | PS | P | FP | F | FS | FSP |
|---|---|---|---|---|---|---|---|
| Average | 370.6 | 380.6 | 387.5 | 388.8 | 388.2 | 423.4 | 424.4 |

(2) Time 1 hr 30

| Cream | S | PS | P | F | FP | FS | FSP |
|---|---|---|---|---|---|---|---|
| Average | 374.7 | 387.8 | 390.3 | 392.3 | 394.4 | 432.3 | 455.0 |

(3) Time 2 hrs

| Cream | S | P | PS | F | FP | FS | FSP |
|---|---|---|---|---|---|---|---|
| Average | 376.2 | 390.3 | 390.6 | 394.4 | 403.7 | 442.8 | 480.9 |

(4) Time 2 hrs 30

| Cream | S | P | F | PS | FP | FS | FSP |
|---|---|---|---|---|---|---|---|
| Average | 376.6 | 385.3 | 391.2 | 392.8 | 405.3 | 454.1 | 481.9 |

The result of these rankings is that cream FS according to the invention after 1 hr 30 min. is significantly lower than cream FSP but it is significantly higher than the other creams after 2 hrs. After 2 hrs 30 min., creams FS and FSP are not significantly different from one another but they are significantly greater than the other creams.

Now we will provide as an illustration without restriction of several examples of vegetable extract-based compositions according to the present invention:

| EXAMPLE 1: Thinning cream | |
|---|---|
| Isopropyl palmitate | 3.0 |
| Soy oil | 6.0 |
| Triple pressure stearic acid | 4.0 |
| Cetyl alcohol | 4.0 |
| Glycerol monostearate | 4.0 |
| Methyl parahydroxybenzoate | 0.2 |
| Propyl parahydroxybenzoate | 0.1 |
| 99% triethanolamine | 0.8 |
| Vegetable extracts: | |
| Dry sage extract (aqueous extract) | 2.0 |
| Dry fragon extract (water-saturated n-butanolic extract) | 2.0 |
| Perfume | 0.3 |
| Sterile deionized water Q.S.P. | 100% by weight |

| EXAMPLE 2: Relaxing body milk for "heavy legs" | |
|---|---|
| Vaseline oil | 16.0 |
| Isopropyl palmitate | 2.0 |
| Liquid lanolin | 1.0 |
| Triple pressure stearic acid | 2.5 |
| Glycerol stearate | 2.5 |
| 99% triethanolamine | 0.8 |
| Methyl parahydroxybenzoate | 0.2 |
| Propyl parahydroxybenzoate | 0.1 |
| Vegetable extracts: | |
| Dry fragon extract (water-saturated | 0.5 |

| EXAMPLE 2: Relaxing body milk for "heavy legs" | |
| --- | --- |
| n-butanolic extract) | |
| Dry sage extract (aqueous extract) | 0.5 |
| Perfume | 0.5 |
| Deionlzed water Q.S.P. | 100% by weight |

| EXAMPLE 3: Relaxing gel for "heavy legs" | |
| --- | --- |
| Polyacrylic acid (Carbopol 940) | 1.0 |
| 99% triethanolamine | 1.0 |
| Propylene glycol | 8.0 |
| Methyl parahydroxybenzoate | 0.1 |
| Propyl parahydroxybenzoate | 0.2 |
| Perfume | 0.3 |
| Vegetable extracts: | |
| Dry fragon extract (water-saturated n-butanolic extract) | 1.5 |
| Sage extract (aqueous extract) | 0.3 |
| Soft hydro-alcoholic passiflore extract | 1.5 |
| Sterile deionized water Q.S.P. | 100% by weight |

| EXAMPLE 4: Cream for roseola | |
| --- | --- |
| Triple pressure stearic acid | 3.0 |
| Cetyl alcohol | 3.0 |
| Glycerol stearate | 3.0 |
| Sorbitan polyoxyethylene mono-oleate | 3.0 |
| Sunflower oil | 10.0 |
| Propylene glycol | 4.0 |
| Sorbitol | 4.0 |
| Methyl parahydroxybenzoate | 0.2 |
| Propyl parahydroxybenzoate | 0.1 |
| Perfume | 0.3 |
| Vegetable extracts: | |
| Dry fragon extract (water-saturated n-butanolic extract) | 0.3 |
| Dry sage extract (aqueous extract) | 0.1 |
| Soft hydroalcoholic passiflore extract (containing 76.5% of solid matter) | 0.1 |
| Sterile deionized water Q.S.P. | 100% by weight |

| EXAMPLE 5: Ointment for varicose veins | |
| --- | --- |
| lsopropyl myristate | 90.5 g |
| Silica (sold as AEROSIL 200 by the DEGUSSA Company) | 8.0 g |
| Vegetable extracts: | |
| Dry fragon extract (water-saturated n-butanolic extract) | 0.5 g |
| Dry sage extract (aqueous extract) | 1.0 g |

| EXAMPLE 6: Suppositories for hemorrhoids (composition per unit) | |
| --- | --- |
| Vegetable extracts: | |
| Dry fragon extract (water-saturated n-butanolic extract) | 0.02 g |
| Dry sage extract (aqueous extract) | 0.02 g |
| Soft hydro-alcoholic passiflore extract (containing 76.5% of solid matter) | 0.02 g |
| Triglycerides of caprylic and capric acids | 0.2 g |
| Semi-synthetic glycerides Q.S.P. | 2.0 g |

What is claimed is:

1. A topical composition for decreasing capillary brittleness, comprising an acceptable carrier and a combination of vegetable extracts comprising:
   (i) A dry *Ruscus aculeatus* L. extract having a saponin content of greater than 65% by weight, wherein said combination of vegetable extracts contains from 0.1 to 3% by weight of said *Ruscus aculeatus* L. extract in relation to the overall weight of the composition, said extract being a hydroalcoholic extract of an alcohol having from 3 to 6 carbon atoms; and
   (ii) A dry *Salvia officinalis* L. extract comprising ursolic acid, flavonoids, rosmarinic acid, picrosalvin and terpenic products, wherein said combination of vegetable extracts contains from 0.1 to 5% by weight of said dry *Salvia officinalis* L. extract in relation to the overall weight of the composition, said extract being selected from the group consisting of an aqueous extract, an alcoholic extract, a hydroalcoholic extract and a propylene glycol extract.

2. The composition of claim 1, further comprising a soft *Passiflora incarnata* extract at a concentration from 0.1 to 2% by weight in relation to the overall weight of the composition, said *Passiflora incarnata* extract being selected from the group consisting of an aqueous extract and a hydroalcoholic extract.

3. The composition of claim 2, wherein said soft *Passiflora incarnata extract* is present at a concentration from 0.2 to 1.5% by weight in relation to the overall weight of the composition.

4. The composition of claim 1, wherein said hydroalcoholic extract of an alcohol having from 3 to 6 carbon atoms is water saturated n-butanol extract.

5. The composition of claim 1, wherein said combination of vegetable extracts contains from 0.3 to 2.5% by weight of said dry *Ruscus aculeatus L.* extract in relation to the overall weight of the composition.

6. The composition of claim 1, wherein said combination of vegetable extracts contains from 0.3 to 3.5% by weight of said dry *Salvia officinalis L.* extract in relation to the overall weight of the composition.

7. The composition of claim 1, wherein in said dry *Ruscus aculeatus L.* extract has a saponin content from 70 to 80% by weight.

8. The composition according to claim 1, wherein said *dry Salvia officinalis L.* extract is an aqueous extract.

* * * * *